(12) United States Patent
Deaver et al.

(10) Patent No.: US 6,387,390 B1
(45) Date of Patent: May 14, 2002

(54) COMPOSITIONS AND METHODS FOR ENHANCING RECEPTOR-MEDIATED CELLULAR INTERNALIZATION

(75) Inventors: Daniel R. Deaver, Franklin; David A. Edwards, Boston, both of MA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/412,821

(22) Filed: Oct. 5, 1999

Related U.S. Application Data
(60) Provisional application No. 60/103,117, filed on Oct. 5, 1998.

(51) Int. Cl.$^7$ ............... A61F 2/02; A61F 13/02; A01K 9/48; A01K 9/20

(52) U.S. Cl. ............ 424/423; 424/434; 424/435; 424/451; 424/464

(58) Field of Search .............. 424/423, 451, 424/464, 430, 434, 435

(56) References Cited

U.S. PATENT DOCUMENTS

| | | |
|---|---|---|
| 4,013,792 A | 3/1977 | Eichmann et al. |
| 4,383,993 A | 5/1983 | Hussain et al. |
| 4,810,503 A | 3/1989 | Carson et al. |
| 5,258,499 A | 11/1993 | Konigsberg et al. |
| 5,766,620 A | 6/1998 | Heiber et al. |

FOREIGN PATENT DOCUMENTS

| | | |
|---|---|---|
| GB | 1090492 A | 11/1967 |
| WO | WO 92/11037 A2 | 7/1992 |
| WO | WO 94/00155 A1 | 1/1994 |
| WO | WO 97/32572 A2 | 9/1997 |

OTHER PUBLICATIONS

Barzu, et al., "Endothelial binding sites for heparin, Specificity and role in heparin neutralization," *Biochem. J.* 238(3):847–54 (1986).

Concise Encyclopedia of Polymer Science and Polymeric Amines and Ammonium Salts, (Goethals, ed.) (Pergamen Press, Elmsford, NY 1980).

Deaver, et al., "Effects of domperidone and thyrotropin–releasing hormone on secretion of luteinizing hormone and prolactin during the luteal phase and following induction of luteal regression in sheep," *Domest. Anim. Endocrinaol.* 4(2):95–102 (1987).

Edwards, et al., "Spontaneous vesicle formation at lipid bilayer membranes," *Biophys. J.* 71(3):1208–14 (1996).

Edwards, et al., "The nucleation of receptor–mediated endocytosis," *Proc. Natl. Acad. Sci. U. S. A.* 93(5): 1786–91, (1996).

Evans & Yeung, "Apparent viscosity and cortical tension of blood granulocytes determined by micropipet aspiration," *Biophys. J.* 56(1):151–60 (1989).

(List continued on next page.)

*Primary Examiner*—Carlos A. Azpuru
(74) *Attorney, Agent, or Firm*—Holland & Knight LLP

(57) ABSTRACT

Compositions and methods for improving cellular internalization of one or more compounds are disclosed. The compositions include a compound to be delivered and a biocompatible viscous material, such as a hydrogel, lipogel, or highly viscous sol. The composition also include, or are administered in conjunction with, an enhancer in an amount effective to maximize expression of or binding to receptors and enhance RME of the compound into the cells. This leads to high transport rates of compounds to be delivered across cell membranes, facilitating more efficient delivery of drugs and diagnostic agents. Compositions are applied topically orally, nasally, vaginally, rectally, and ocularly. The enhancer is administered with the composition or separately, either systemically or preferably locally. The compound to be delivered can also be the enhancer.

22 Claims, 5 Drawing Sheets

OTHER PUBLICATIONS

Goldstein, et al., "Receptor–mediated endocytosis: concepts emerging from the LDL receptor system," *Annu. Rev. Cell. Biol.* 1:1–39 (1985).

Illum. et al., "Bioadhesive Microspheres as a Potential Nasal Drug Delivery System," *Int. J. Pharm.* 39:189–199 (1987).

Mandal, et al., "Physiochemical studies on achatininH, a novel sialic acid–binding lectin," *Biochem. J.* 257(1):65–71 (1989).

Pagano, "Lipid traffic in eukaryotic cells: mechanisms for intracellular transport and organelle–specific enrichment of lipids," *Curr. Opin, Cell. Biol.* 2(4):652–63 (1990).

Rodman, et al., "Endocytosis and transcytosis," *Curr. Opin. Cell. Biol.* 2(4):664–72 (1990).

Schmid, "Biochemical requirements for the formation of clathrin–and COP–coated transport vesicles," *Curr. Opin. Cell. Biol.* 5(4):621–7 (1993).

Sheetz, & Dai, (1995), "Modulation of membrane dynamics and cell motility by membrane tension," 60th Annual Cold Spring Harbor Symposium on Protein Kinases, Cold Spring Harbor, N.Y.

Smythe, et al., "Cytosol–and clathrin–dependent stimulation of endocytosis in vitro by purified adaptors," *J. Cell. Biol.* 119(5):1163–71 (1992).

Smythe, et al., "Formation of coated vesicles from coated pits in broken A431 cells," *J. Cell. Biol.* 108(3):843–53.

Trowbridge, "Endocytosis and signals for internalization," *Curr. Opin. Cell. Biol.* 3(4):634–41 (1991).

Wang, et al., "Mechanotransduction across the cell surface and through the cytoskeleton," *Science* 260(5111):1124–7 (1993).

Wright & Detmers, "Receptor–mediated phagocytosis" in *The Lung: Scientific Foundations* (Crystal, et al., eds.), pp. 539–49 (Ravens Press, Ltd., New York, NY(1991).

COMPOSITIONS AND METHODS FOR ENHANCING RECEPTOR-MEDIATED CELLULAR INTERNALIZATION

CROSS-REFERENCE TO RELATED APPLICATIONS

Priority is claimed to U.S. provisional application Ser. No. 60/103,117, filed Oct. 5, 1998.

BACKGROUND OF THE INVENTION

The compositions and methods of use described herein generally are in the field of materials and methods for enhancing cellular internalization.

It is often difficult to deliver compounds, such as proteins, peptides, genetic material, and other drugs and diagnostic compounds intracellularly because cell membranes often resist the passage of these compounds. Various methods have been developed to administer agents intracellularly. For example, genetic material has been administered into cells in vivo, in vitro, and ex vivo using viral vectors, DNA/lipid complexes, and liposomes. While viral vectors are efficient, questions remain regarding the safety of a live vector and the development of an immune response following repeated administration. Lipid complexes and liposomes appear less effective at transfecting DNA into the nucleus of the cell and potentially may be destroyed by macrophages in vivo.

Proteins and peptides are typically administered by parenteral administration, or, in some cases, across the nasal mucous membrane. Uptake of drugs administered topically is frequently poor, and degradation frequently occurs when drugs are administered orally. For example, hormones such as gonadotropin releasing hormone ("GnRH") and its analogs have been administered to humans in an attempt to increase fertility by increasing systemic levels of luteinizing hormone ("LH"). When given often, low doses of native GnRH have been shown to induce follicular development and ovulation. These drugs are typically administered via an indwelling catheter into the abdominal cavity. An external pump is attached to the catheter which injects the peptide at frequent intervals. This method of administration is extremely invasive and undesirable. Also, the method is prohibitively expensive for use in animals.

It has recently been demonstrated that, by embedding individual cell populations in hydrogel media of macroscopic viscosity similar to that characteristic of cell cytoskeleta, the rate of receptor-mediated endocytosis can be significantly enhanced (Edwards, et al., *Proc. Natl. Acad. Sci. U.S.A.* 93:1786–91 (1996); PCT US97/03276 by Massachusetts Institute of Technology and Pennsylvania State University Foundation). This enhancement effect appears to reflect a fluid-mechanical origin of receptor-mediated endocytosis, involving the rapid expansion of plasma membrane in the vicinity of a receptor cluster leading to an invaginating membrane motion that is sensitive to the viscous properties of the extracellular environment (Edwards, et al., *Proc. Natl. Acad. Sci. U.S.A.* 93:1786–91 (1996); Edwards, et al., *Biophys. J.* 71:1208–14 (1996)).

It has been found, however, that the delivery of compounds via a receptor-mediated route into the systemic circulation by noninvasively delivering the compound in a "rheologically-optimized" hydrogel may be inconsistent or poorly reproducible. It would be advantageous to better understand the role of RME in uptake of compounds in order to develop improved methods of delivery of compounds, such as drugs, intracellularly.

The binding of ligands or assembly proteins to surface receptors of eucaryotic cell membranes has been extensively studied in an effort to develop better ways to promote or enhance cellular uptake. For example, binding of ligands or proteins has been reported to initiate or accompany a cascade of nonequilibrium phenomena culminating in the cellular invagination of membrane complexes within clathrin-coated vesicles (Goldstein, et al., *Ann. Rev. Cell Biol.* 1:1–39 (1985); Rodman, et al., *Curr. Op. Cell Biol.* 2:664–72 (1990); Trowbridge, *Curr. Op. Cell Biol.* 3:634–41 (1991); Smythe, et al., *J. Cell Biol.* 108:843–53 (1989); Smythe, et al., *J. Cell Biol.* 119:1163–71 (1992); and Schmid, *Curr. Op. Cell Biol.* 5:621–27 (1993)). This process has been referred to as receptor-mediated endocytosis ("RME"). Beyond playing a central role in cellular lipid trafficking (Pagano, *Curr. Op. Cell Biol.* 2:652–63 (1990)), RME is the primary means by which macromolecules enter eucaryotic cells.

An effective strategy for enhancing the uptake of cytotoxic and therapeutic drugs involves exploiting the rapidity and specificity of transmembrane transport via receptor-mediated endocytosis (Goldstein, et al., *Ann. Rev. Cell Biol.* 1:1–39 (1985)) by targeting receptors on the plasma membranes of endothelial (Barzu, et al., *Biochem. J.* 15;238(3):847–854 (1986); Magnusson & Berg, *Biochem. J.* 257:65–56 (1989)), phagocytic (Wright & Detmers, "Receptor-mediated phagocytosis" in *The Lung: Scientific Foundations* (Crystal, et al., eds.), pp. 539–49 (Ravens Press, Ltd., New York, N.Y.(1991)); and tumor cells, as well as cells of other tissues. Receptor targeting has, however, not been championed as a means of avoiding intravenous injection of hard-to-absorb macromolecules, probably because macromolecules often degrade prior to reaching receptors in the gastrointestinal tract following oral administration, and do not appear to require receptor-mediation to permeate across the alveolar epithelium following inhalation. Other noninvasive macromolecular drug delivery strategies either do not expose receptors to the topical environment, for example transdermal delivery, or have been less extensively explored, such as nasal delivery (Illum, et al., *Int. J. Pharm.* 39:189–99 (1987)), vaginal delivery, or ocular delivery.

It is therefore an object of the present invention to provide compositions and methods for enhancing intracellular delivery of bioactive and/or diagnostic agents, especially steroidal compounds and materials which are endocytosed by a receptor-mediated mechanism.

SUMMARY OF THE INVENTION

Compositions and methods for improving cellular internalization of one or more compounds using a receptor mediated mechanism are disclosed. The compositions include a compound to be delivered and a biocompatible viscous material, such as a hydrogel, lipogel, or highly viscous sol, and are administered subsequent to or with steroid or other material binding to the receptor at the site of application to enhance uptake (referred to as an "enhancer"). By controlling the apparent viscosity of the viscous materials, the rates of endocytosis, including nonspecific "pinocytosis" and specific RME, are increased. The rate of endocytic internalization is increased when the ratio of the apparent viscosities of cytosolic and extracellular media approaches unity. The composition includes, or is co-administered with, the enhancer, usually a steroid or other molecule binding to receptors at the site of application in an amount effective to maximize binding to the receptors or expression of receptors and enhance RME of the compound into the cells. This leads to high transport rates of compounds to be delivered across cell membranes, facilitating more efficient delivery of drugs and diagnostic agents.

Preferred viscous materials are hydrogels, lipogels (gels with nonaqueous fluid interstices) and highly viscous sols. The apparent viscosity of the composition is controlled such that it lies in the range of between 0.1 and 2000 Poise, preferably between 7 and 1000 Poise, and most preferably between 2 and 200 Poise. Compounds to be delivered include those that can be attached, covalently or noncovalently, to a molecule that either stimulates RME or pinocytosis by binding to receptors on the plasma membrane, binds specifically to receptors that undergo RME or pinocytosis independently of this binding (i.e., which are themselves "enhancers") or at least can be associated chemically or physically with other molecules or "carriers" that themselves undergo RME or pinocytosis. Exemplary compounds to be delivered include proteins and peptides, nucleotide molecules, saccharides and polysaccharides, synthetic chemotherapeutic agents, and diagnostic compounds. The examples demonstrate the roles of estrogen and progesterone in vaginal delivery of peptide hormones. Peptide transport into the systemic circulation is strongly steroid-dependent, with most efficient transport of reproductive hormones occurring after estradiol and progesterone pretreatment, when hormone receptors are maximally expressed. Preferred steroids include steroidal hormones such as estrogen and progesterone and glucocorticoids.

The compositions are applied to cell membranes to achieve high rates of transport of the compound to be delivered across those membranes, relative to when non-viscous fluids are used with the enhancers or the viscous fluids are used alone. Compositions are applied topically orally, nasally, vaginally, rectally, and ocularly. The enhancer is administered systemically or, more preferably, locally. Compositions can be applied by injection via catheter, intramuscularly, subcutaneously, and intraperitoneally. Compositions can also be administered to the pulmonary or respiratory system, most preferably in an aerosol.

BRIEF DESCRIPTION OF THE DRAWINGS

FIG. 1a shows serum cortisol response to iv injection and vaginal administration of vasopressin. Vasopressin was injected intravenously (5 $\mu$g dose) through a jugular catheter. The peptide was delivered vaginally in 5 ml of aqueous solution (200 $\mu$g dose). Standard errors are based on n=6. FIG. 1b shows Serum LH response to iv injection and vaginal administration of leuprole acetate ("LHRH analog"). LHRH analog was injected intravenously (5 $\mu$g dose) into through a jugular catheter. The peptide was delivered vaginally in 5 ml of aqueous solution (200 $\mu$g dose). Standard errors are based on n=6.

DETAILED DESCRIPTION OF THE INVENTION

Figure 1A:
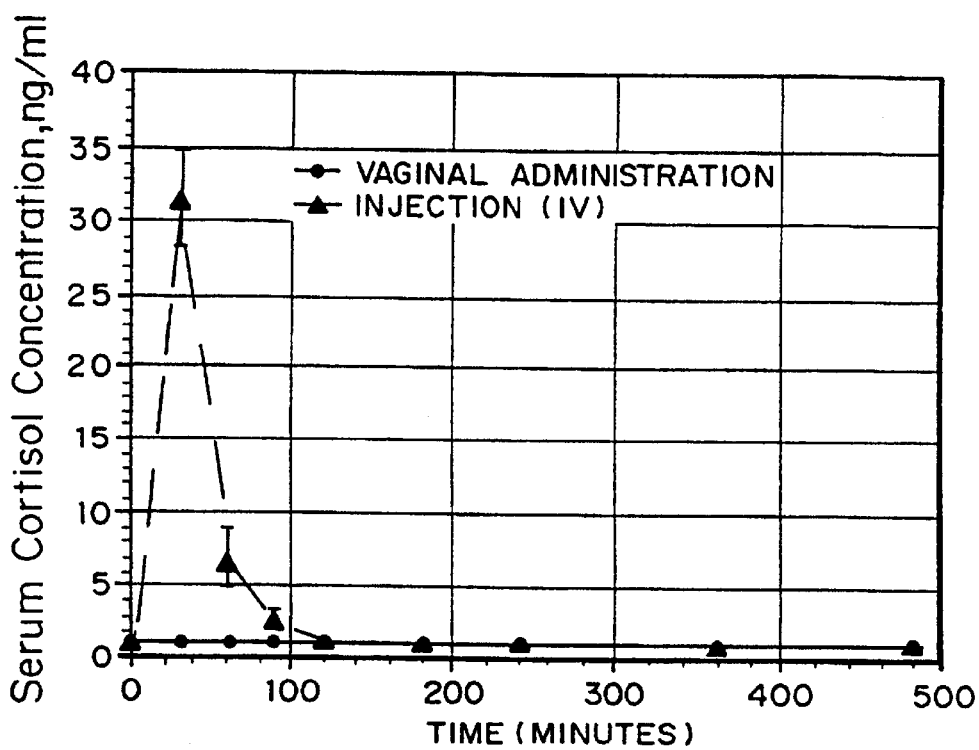
FIGS. 1a and 1b are graphs showing serum responses to iv injection and vacinal administration of vasopressin and leuprolide acetate.

Compositions and methods for intracellular delivery of compounds in a iscous solution enhancing uptake are described. Cellular internalization is enhanced (1) by increasing the rate of receptor-mediated endocytosis by controlling the viscosity of the solution containing the compound to be delivered and (2) by co-administration of an enhancer (such as a steroid) in an amount effective to maximize expression of or binding to receptors involved in endocytosis mediated uptake. The compositions include one or more bioactive or diagnostic compounds and a fluid with an apparent viscosity approximately equal to the apparent viscosity of the cytosolic fluid in the cell to which the composition is administered, and optionally, the enhancer. The enhancer can be delivered in the same formulation or separately, before or after administration of the compounds to be delivered to the site where they are to be delivered. Alternatively, the compound can be administered in the viscous carrier solution at a time selected to maximize relevant steroidal levels, for example, administered vaginally during estrus.

Preferably, the compound binds to or otherwise interacts with receptors on the surface of the cell to which it is to be delivered. If the compound does not itself bind to or interact with receptors on the cell surface, it can be administered in a viscous fluid that also includes a carrier for the compound. The carrier contains ligands that bind to or otherwise interact with cell surface receptors, which allows compounds that do not bind to or otherwise interact with cell surface receptors to participate in RME.

Compositions

The binding of ligands or assembly proteins to surface receptors of eucaryotic cell membranes initiates or accompanies a cascade of nonequilibrium phenomena culminating in the cellular invagination of membrane complexes within clathrin-coated vesicles. This process is known as receptormediated endocytosis (RME). RME is the primary means by which several types of bioactive molecules, particularly macromolecules, enter eukaryotic cells.

Research by others has primarily focused on the identification and biochemical characterization of the early and later stages of RME, ranging from formation of a clathrin coated pit to snap-off of a coated vesicle. Determination of the compositions and methods for intracellularly administering compounds described herein involved focusing on a different aspect of RME, the process in which a membrane depression is initially formed at the outset of RME (i.e. the mechanism by which a spontaneous thrust of the cell membrane toward the cytosol occurs). This process is referred to herein as the 'nucleation stage' of RME. This terminology is intended to emphasize that the driving force for the spontaneous thrust of the membrane toward the cytosol is related to energy liberated by one or more of many possible exothermic membrane-binding reactions, i.e., receptor-ligand binding, that precede or accompany formation of a membrane depression.

Cell membranes are bound from without by extracellular fluid and from within by cytosolic fluid. The inter- and extracellular fluids possess different physical properties, such as density and fluid viscosity, whose values extend up to the membrane surface where they undergo discontinuities. The membrane itself possesses unique equilibrium and nonequilibrium properties. An important property when considering intracellular delivery is the membrane tension (the free energy of the membrane per unit surface area). Membrane tension is generally uniform and positive at an equilibrium membrane and can be measured by routine micropipet experiments. Most reported membrane tension values have been gathered for red blood cells, and range from 4 dyne/cm to 0.01 dyne/cm. By contrast, the interfacial tension of an air/water interface is 73 dyne/cm. Membrane tension can vary from point to point on the membrane surface as a consequence of various stimuli, such as non-uniform heating of the membrane, membrane chemical reactions and membrane compositional changes. These variations can give rise to membrane and bulk-fluid motion, tenned Marangoni convection. This motion is characterized for the most part by cytosolic and extracellular (apparent) viscosities.

Exothermic reactions can occur on the cell membrane, due to ligand-recptor binding, adaptor-membrane binding, clathrin-membrane binding, a combination of these binding reactions, and other membrane reactions. The exothermic reactions cause the membrane tension (energy per membrane area), at least momentarily, to be diminished at the point where the reaction occurred. As the membrane tension is lowered, the configurational and intermolecular potential energies of membrane-bound molecular complexes are also lowered.

The cell membrane tension is spatially nonuniform as a consequence of the exothermic reactions (i.e., membrane complex formation), resulting in membrane motion. This motion will possess a substantial component toward the cell cytosol so long as the cytosolic viscosity exceeds that of the extracellular fluid.

This membrane motion causes membrane deformation, an event resisted by the membrane tension. When the differences between the apparent viscosities of the cytosolic fluid and the extracellular fluid are extremely large, membrane deformation is strongly resisted and the initial thrust of the membrane is damped. However, as the differences between the apparent viscosities of the cytosolic fluid and the extracellular fluid become extremely small, membrane deformation becomes progressively rapid.

Accordingly, the rate of endocytosis can be increased by adjusting the viscosity of the extracellular fluid so that it is approximately the same as that of the cytosolic fluid, as described by PCT/US97/03276. If the viscosity of the extracellular fluid is appreciably higher or lower than that of the cytosolic fluid, the rate of endocytosis decreases. This was shown experimentally in Example 1 and FIG. 3 of PCT US97/03276, in which the ratio of compounds that were internalized to those remaining on the surface (In/Sur) increased as the viscosity of the extracellular fluid increased, to a point at which the viscosity approached that of the cytosolic fluid. Above that value, the ratio decreased.

Clustering of membrane complexes is favorable for rapid internalization. The rate of internalization can be increased in proportion to the magnitude of binding energy. This is due, in part, to the specificity of receptors to particular ligands and/or adaptor proteins.

Clustering of complexes occurs in the vicinity of pits to which clathrin triskelions absorb from the cytosolic side of the cell membrane and subsequently polymerize to form a clathrin coat. Some clustering has also been observed in the vicinity of caveolac, or non-clathrin-coated pits. The membrane-tension depression occurring within the vicinity of an evolving pit, originating in the process of membrane complexation, is directly proportional to the number of membrane complexes formed within that pit. In general, clustered complexes have been found to internalize substances more rapidly than nonclustered complexes.

The magnitudes of apparent viscosity difference and receptor clustering have each been found to alter the rate of RME. Membrane tension can also be manipulated to influence the rate of RME. Increasing the membrane tension 'hardens' the cell membrane, making cell membrane depression increasingly prohibitive. This phenomenon has been commented upon by Sheetz, M.P. and Dai, J. (1995), presented at the 60*th Annual Cold Spring Harbor Symposium on Protein Kinases*, Cold Spring Harbor, N.Y., on the basis of studies that show an increased rate of endocytosis for neuronal growth cones coinciding with membrane tension lowering.

Accordingly, the rate of internalization can be increased by a) adjusting the viscosity of the extracellular fluid to approximate that of the cytosolic fluid; b) forming complexes of the material to be internalized; and c) reducing membrane tension. Compositions and methods for increasing the rate of endocytosis are described in detail below.

A. Viscous Hydrogels

Suitable viscous fluids for use in intracellularly administering compounds include biocompatible hydrogels, lipogels, and highly viscous sols.

A hydrogel is defined as a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides, proteins and synthetic polymers. Examples of polysaccharides include celluloses such as methyl cellulose, dextrans, and alginate. Examples of proteins include gelatin and hyaluronic acid. Examples of synthetic polymers include both biodegradeable and non-degradeable polymers (although biodegradeable polymers are preferred), such as polyvinyl alcohol, polyacrylamide, polyphosphazines, polyacrylates, polyethylene oxide, and polyalkylene oxide block copolymers ("POLOXAMERS™") such as PLURONICS™ or TETRONICS™ (polyethylene oxide-polypropylene glycol block copolymers).

In general, these polymers are at least partially soluble in aqueous solutions, such as water, buffered salt solutions, or aqueous alcohol solutions. Several of these have charged side groups, or a monovalent ionic salt thereof. Examples of polymers with acidic side groups that can be reacted with cations are polyphosphazenes, polyacrylic acids, poly(meth) acrylic acids, polyvinyl acetate, and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions arc polyvinyl amines, polyvinyl pyridine, polyvinyl imidazole, polyvinylpyrrolidone and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix. An aqueous solution containing the compound to be delivered can be suspended in a solution of a water soluble polymer, and the suspension can be formed into droplets which are configured into discrete microcapsules by contact with multivalent cations. Optionally, the surface of the microcapsules can be crosslinked with polyamino acids to form a semipermeable membrane around the encapsulated materials.

The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups. For example, a polyanionic poly[bis(carboxylatophenoxy)] phosphazenc (PCPP) can be synthesized, which is cross-linked with dissolved multivalent cations in aqueous media at room temperature or below to form hydrogel matrices.

Methods for the synthesis of the polymers described above are known to those skilled in the art. See, for example *Concise Encyclopedia of Polymer Science* and *Polymeric Amines and Ammonium Salts*, (Goethals, ed.) (Pergamen Press, Elmsford, N.Y. 1980). Many of these polymers are commercially available.

Preferred hydrogels include aqueous-filled polymer networks composed of celluloses such as methyl cellulose, dextrans, agarose, polyvinyl alcohol, hyaluronic acid, polyacrylamide, polyethylene oxide and polyoxyalkylene polymers ("poloxamers"), especially polyethylene oxide-polypropylene glycol block copolymers, as described in U.S. Pat. No. 4,810,503. Several poloxamers are commercially available from BASF and from Wyandotte Chemical Corporation as "Pluronics". They are available in average molecular weights of from about 1100 to about 15,500.

As used herein, lipogels are gels with nonaqueous fluid interstices. Examples of lipogels include natural and synthetic lecithins in organic solvents to which a small amount of water is added. The organic solvents include linear and cyclic hydrocarbons, esters of fatty acids and certain amines (Scartazzini et al. *Phys. Chem.* 92:829–33 (1988)).

As defined herein, a sol is a colloidal solution consisting of a liquid dispersion medium and a colloidal substance which is distributed throughout the dispersion medium. A highly viscous sol is a sol with a viscosity between approximately 0.1 and 2000 Poise.

Other useful viscous fluids include gelatin and concentrated sugar (such as sorbitol) solutions with a viscosity between approximately 0.1 and 2000 Poise.

The apparent viscosity of the extracellular fluid (the composition) must be approximately equal to the viscosity of the cytosolic fluid in the cell to which the compounds are to be administered. One of skill in the art can readily determine or reasonably estimate of the viscosity of the cytosolic fluid using a viscometer and measuring the applied stress divided by measured strain rate at the applied stress that corresponds to the stress the cell membrane imparts upon the cytosolic and extracellular fluids during endocytosis. Methods for measuring the cytosolic viscosity include micropipette methods (Evans & Young, *Biophys. J.*, 56:151–160 (1989)) and methods involving the motion of membrane-linked colloids (Wang et al., *Science*, 260:1124–26 (1993). Typical cytosol viscosities, measured by these techniques, range from approximately 50–200 Poise. Once this value is measured, the viscosity of the composition can be adjusted to be roughly equal to that viscosity, particularly when measured via routine methods at the applied stress that corresponds to the stress the cell membrane imparts upon the cytosolic and extracellular fluids during endocytosis.

The viscosity can be controlled via any suitable method known to those of skill in the art. The method for obtaining a viscous composition with the desired apparent viscosity is not particularly limited since it is the value of the apparent viscosity relative to the target cells which is critical. The apparent viscosity can be controlled by adjusting the solvent (i.e., water) content, types of materials, ionic strength, pH, temperature, polymer or polysaccharide chemistry performed on the materials, and/or external electric, ultrasound, or magnetic fields, among other parameters.

The apparent viscosity of the compositions is controlled such that it lies in the range of between 0.1 and 2000 Poise, preferably between 7 and 1000 Poise, and most preferably between 2 and 200 Poise. The apparent viscosity can be measured by a standard rheometer using an applied stress range of between 1 and 1000 Pascals, preferably between 1 and 500 Pascals, and most preferably between 1 and 100 Pascals. Further, the viscosity of the compositions is controlled so that the quotient of (apparent viscosity of the cytosol of the target cells-apparent viscosity of the composition) and the apparent viscosity of the cytosol of the target cells is between approximately −0.1 and 0.3, preferably between approximately 0 and 0.3, more preferably between approximately 0 and 0.1, and most preferably between approximately 0 and 0.05.

The composition can be administered as an only slightly viscous formulation that becomes more viscous in response to a condition in the body, such as body temperature or a physiological stimulus, like calcium ions or pH, or in response to an externally applied condition, such as ultrasound or electric or magnetic fields. An example is a temperature sensitive poloxamer which increases in viscosity at body temperature.

The following are examples of suitable concentration ranges: Methocel solutions in the range of between 1.0 and 2.0% (w/w), polyvinyl alcohol solutions between 5 and 15%, pluronic acid solutions between 15 and 20% and trehalose solutions between 1 and 5%.

B. Enhancers

Compounds that can be attached, covalently or noncovalently, to a molecule that either stimulates receptormediated endocytosis (RME) or pinocytosis by binding to receptors on the plasma membrane, binds specifically to receptors that undergo RME or pinocytosis independently of this binding, or at least can be associated chemically or physically with other molecules or "carriers" that themselves undergo RME or pinocytosis, are referred to as enhancers for intracellular delivery. Examples include steroids such as estradiol and progesterone, and some glucocorticoids. Glucocorticoids such as dexamethasone, cortisone, hydrocortisone, prednisone, and others are routinely administered orally or by injection. Other glucocorticoids include beclomethasone, dipropianate, betamethasone, flunisolide, methyl prednisone, para methasone, prednisolone, triamcinolome, alclometasone, amcinonide, clobetasol, fludrocortisone, diflurosone diacetate, fluocinolone acetonide, fluoromethalone, flurandrenolide, halcinonide, medrysone, and mometasone, and pharmaceutically acceptable salts and mixtures thereof. Other compounds also bind specifically to receptors on cell surfaces. Many hormone specific receptors are known. These can all be used to enhance uptake. Selection of molecules binding to receptors which are predominantly found on a particular cell type or which are specific to a particular cell type can be used to impart selectivity of uptake.

The enhancer is preferably administered at a time and in an amount effective to maximize expression of receptors, and consequently receptor mediated internalization of the compound. The enhancer can itself be the compound to be delivered.

C. Compounds to be Delivered

As noted above, the compound to be delivered may be the same as or different from the enhancer. The enhancer can be administered as part of the formulation containing the compound to be delivered or prior to or as part of a different formulation. The enhancer may be administered systemically, followed by administration of the compound to be delivered directly to the site where uptake is to occur.

Compounds to be delivered include proteins and peptides, nucleic acid molecules including DNA, RNA, antisense oligonucleotides, triplex forming materials, ribozymes, and guide sequences for ribozymes, carbohydrates and polysaccharides, lipids, and other synthetic organic and inorganic molecules. Preferred bioactive compounds include growth factors, antigens, antibodies or antibody fragments, and genes such as genes useful for treatment of cystic fibrosis, A1A deficiency and other genetic deficiencies.

Preferred hormones includes peptide-releasing hormones such as insulin, luteinizing hormone releasing hormone ("LHRH"), gonadotropin releasing hormone ("GnRH"), deslorelin and leuprolide acetate, oxytocin, vasoactive intestinal peptide (VIP), glucagon, parathyroid hormone (PTH), thyroid stimulating hormone, follicle stimulating hormone, growth factors such as nerve growth factor (NGF), epidermal growth factor (EGF), vascular endothelial growth factor (VEGF), insulin-like growth factors (IGF-I and IGF-II), fibroblast growth factors (FGFs), platelet-derived endothelial cell growth factor (PD-ECGF), transforming growth factor beta (TGF-$\beta$), and keratinocyte growth factor (KGF). Other materials which can be delivered include cytokines such as tumor necrosis factors (TFN-$\alpha$ and TNF-$\beta$), colony stimulating factors (CSFs), interleukin-2, gamma interferon, consensus interferon, alpha interfercrons, beta interferon; attachment peptides such as RGD; bioactive peptides such as renin inhibitory peptides, vasopressin, detirelix, somatostatin, and vasoactive intestinal peptide; coagulation inhibitors such as aprotinin, heparin, and hirudin; enzymes such as superoxide dismutase, neutral endopeptidase, catalase, albumin, calcitonin, alpha-1-antitrypsin (A1A), deoxyribonuclease (DNAase), lectins such as concanavalin A, and analogues thereof.

Diagnostic agents can also be delivered. These can be administered alone or coupled to one or more bioactive compounds as described above. The agents can be radiolabelled, fluorescently labeled, enzymatically labeled and/or include magnetic compounds and other materials that can be detected using x-rays, ultrasound, magnetic resonance imaging ("MRI"), computed tomography ("CT"), or fluoroscopy.

D. Carriers for Compounds to be Delivered

The compounds to be delivered and/or enhancers can optionally be incorporated into carriers, which are then dispersed in a viscous fluid with an apparent viscosity approximately equal to the cytosolic fluid of the cell to which the compounds are to be delivered. Exemplary carriers include viruses, liposomes, lipid/DNA complexes, micelles, protein/lipid complexes, and polymeric nanoparticles or microparticles.

The carrier must be small enough to be effectively endocytosed. Suitable carriers possess a characteristic dimension of less than about 200 nm, preferably less than about 100 nm, and more preferably, are less than about 60 nm.

The carrier must be able to bind to a cell surface receptor. If the carrier does not naturally bind, it is well known in the art how to modify carriers such that they are bound, ionically or covalently, to a ligand (i.e., LHRH) that binds to a cell surface receptor. For example, U.S. Pat. No. 5,258,499 to Konigsberg et al. describes the incorporation of receptor specific ligands into liposomes, which are then used to target receptors on the cell surface.

The use of carriers can be important when the compound to be delivered does not bind to or otherwise interact with cell surface receptors. The compound can be incorporated into a carrier which contains a ligand or other moiety which binds to or interacts with cell surface receptors. Then, due to the binding of or interaction with the receptor to the cell surface and the apparent viscosity of the composition, the carrier (and encapsulated compound) is intracellularly delivered by endocytosis.

The use of carriers can be particularly important for intracellularly delivering nucleic acid molecules. In one embodiment, nucleic acid molecules are encapsulated in a liposome, preferably a cationic liposome, that has a receptor-binding ligand, such as LHRB, on its surface. The liposome is then dispersed in a viscous fluid. When the composition is administered, the liposomes are endocytosed by the cell, and the nucleic acid molecules are released from the liposome inside the cell.

E. Compositions for Lowering or Raising Membrane Tension

The efficiency of the method can be increased by lowering the membrane tension. Suitable methods for lowering membrane tension include including a biocompatible surface active agent in the hydrogel, performing exothermic reactions on the cell surface (i.e., complex formnation), and applying an external field to the cell surface. Suitable biocompatible surface active agents include surfactin, trehalose, fatty acids such as palmitin and oleic acid, polyethylene glycol, hexadecanol, and phospholipids such as phosphatidylcholines and phosphatidylglycerols. Suitable complex-forming chemical reactions include the reaction of receptor-binding ligands with cell surface receptors for these ligands, exothermic reactions such as occur between sodium salicylate and salicylic acid, and neutralization reactions as between hydrochloric acid and ammonia (Edwards et al. 1996 *Biophys. J.* 71, 1208–1214). External fields that can be applied to a cell surface to reduce membrane tension include ultrasound, electric fields, and focused light beams, such as laser beams.

The rate of cellular internalization can also be increased by causing the clustering of receptors on the cell membrane. This can be accomplished, for example, by creating zones on the membrane where the membrane tension is relatively high, causing the membrane fluid to flow toward the zone of high membrane tension. This flow can carry receptors localized in the membrane toward each other, causing them to cluster.

Methods of Administration

In a preferred embodiment, the compound to be delivered and/or the enhancer are contained in the same formulation for simultaneous administration. Alternatively, the composition and steroid are provided as parts of a kit, for separate administration. As shown in the examples, the enhancer may be a hormone such as estradiol or progesterone, administered systemically, while the compound to be delivered is administered topically at a site where delivery is enhanced by the hormone, such as the vaginal mucosa.

The compositions can be applied topically to the vagina, rectum, nose, eye, ear, mouth and the respiratory or pulmonary system. Preferably, the compositions are applied directly to the cells to which the compound is to be delivered, usually in a topical formulation. The enhancer can be administered simultaneously with or after administration of the composition including the viscous gel and agent to be delivered. The administration schedule (e.g., the interval of time between administering the enhancer and administering the gel composition) can be readily selected by one of skill in the art to maximize receptor expression and/or binding before exposure of the cell surface to the agent to be delivered.

The compositions are particularly advantageous for gene delivery and hormone therapy By delivering a composition containing peptides such as GnRH or its analogues across the vaginal or nasal membranes, the compositions can be used to treat a variety of human hormone-based disorders.

The dosage will be expected to vary depending on several factors, including the patient, the particular bioactive compound to be delivered, and the nature of the condition to be treated, among other factors. One of skill in the art can readily determine an effective amount of the bioactive compound or compounds to administer to a patient in need thereof.

The method involves administering the composition to cells to enhance the rate of transport across the cell membranes, relative to the rate of delivery when non-viscous fluids are used in combination with enhancer or when viscous fluids are used without enhancer. Examples of methods of administration include oral administration, as in a liquid formulation or within solid foods, topical administration to the skin or the surface of the eye, intravaginal administration, rectal administration, intranasal administration, and administration via inhalation. When the composition is administered orally or by inhalation, it is preferred that it is administered as a dry powder that includes a swellable hydrogel that is designed to swell to an appropriate viscosity after delivery to the desired location. After inhalation, for example, the hydrogel absorbs water to obtain the desired viscosity and then delivers agents to the respiratory system. When administered orally, a hydrogel can be selected that does not absorb water under conditions present in the upper gastrointestinal tract, but which does absorb water under conditions present in the lower gastrointestinal tract (i.e., at a pH greater than about 6.5). Such hydrogels are well known to those of skill in the art. The use of such compositions can optimize the delivery of agents to the lower gastrointestinal tract.

Applications for the Compositions and Methods

The methods and compositions described herein are useful in a variety of therapeutic and diagnostic applications for humans and other animals. Preferred applications include the treatment of infertility and disease, such as cancer. The compositions can be used in various hormone replacement therapies as well. In a preferred method of use, viscous compositions arc used to deliver progesterone vaginally to induce secretory transformation of the endometrium and promote development of pregnancy.

The compositions and methods of use thereof described herein will be more clearly understood with reference to the following non-limiting examples.

EXAMPLE 1

Peptide Transport Across the Vaginal Epithelium of Sheep

This study was intended to examine the relevance of control of the apparent viscosity of the extracellular fluid/cytosolic fluid to the enhancement of peptide drug delivery into the body via a noninvasive route by examining peptide transport across the vaginal epithelium of sheep.

A. Receptor-mediated Transport of a Peptide, No Exogenous Steroid

First, a peptide that undergoes receptor-mediated transport across the vaginal epithelium was identified by studying the permeation of peptides of varying molecular weight in a sheep model. Peptides were delivered vaginally to sheep in 5 ml of aqueous or methocel solutions with typical peptide concentrations of 10–40 $\mu$g/ml. A group of 18 intact ewes were utilized for these experiments. For each study, sheep were randomly assigned to a treatment group. In GNRH studies where each animal received all possible treatment combinations, each animal was assigned to an initial treatment group at random and subsequently randomly to each of the remaining treatment groups. A minimum of 5 days (typically 10 or more days) was allowed between experiments on a given animal, to provide sufficient time for complete recovery of pituitary responsiveness to the highest doses of the GnRH agonist used. A 16G 150 mm jugular catheter (Abbocath-T, Abbott Laboratories, Chicago, Ill.) was inserted and blood samples collected at 0, 30, 60, 90, 120, 180, 240, 360, 480 and 1440 min. after treatment. Luteinizing hormone (LH) levels were determined.

Figure 1B:
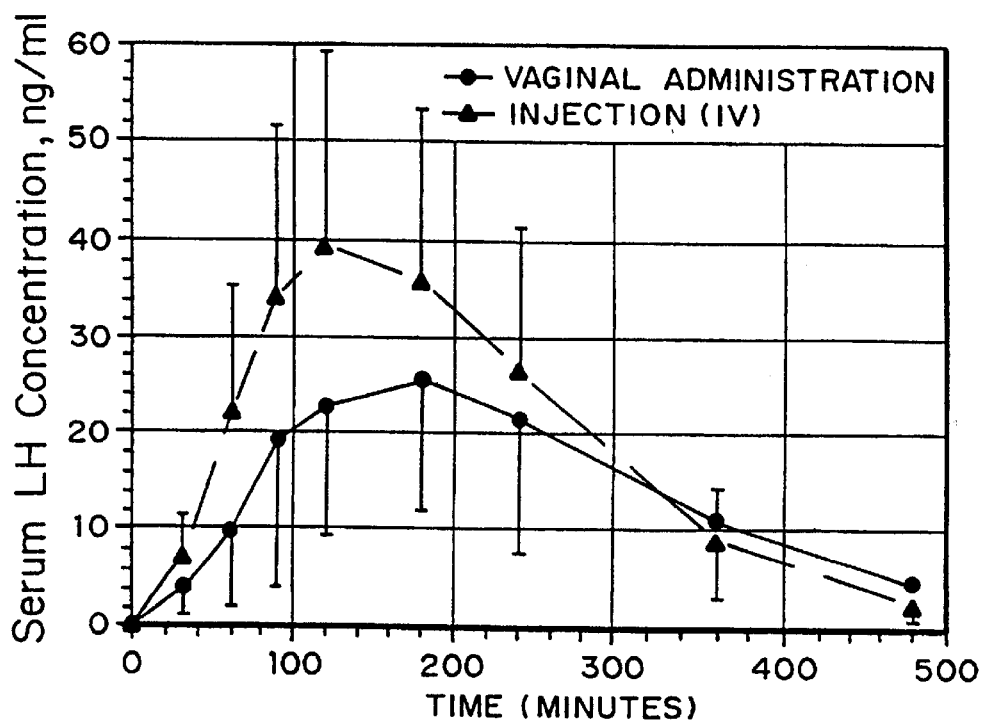

The bioavailabilities of vasopressin (1084 Da), salmon calcitonin (3416 Da), and insulin (5786 Da) all were found to be less than 0.1% following vaginal administration in an aqueous buffer. Leuprolide acetate [luteinizing hormone releasing hormone (LHRH) analog] (1209 Da), however, exhibited high bioavailability (2.6±0.9%) based on biological response, even though its molecular weight is slightly larger than that of vasopressin. A comparison of the biological response to vasopressin and Icuprolide acetate is shown in FIGS. 1a and 1b. Vasopressin administered by intravenous injection leads to high systemic cortisol levels within the first hour following treatment. However no detectable change in systemic cortisol levels was observed following vaginal administration (FIG. 1a). In contrast, LHRH analog produced significant luteinizing hormone (LH) response following intravenous injection and following vaginal administration (FIG. 1b). The near coincidence of peak serum LH concentrations following injection and vaginal administration indicated rapid internalization of leuprolide acetate, characteristic of a receptor-mediated route of transport.

B. Enhancement of Transport using a Viscous, Balanced Carrier

LHRH analog was placed in methyl cellulose solutions ("methocels") of varying apparent viscosity. Studies of transferrin-mediated endocytosis on single cells have shown peak endocytosis rates at methyl cellulose concentrations between 1.25 and 1.75%, at which concentrations the methocels exhibit apparent viscosities in a range typical of intracellular viscosities (Evans & Yeung, *Biophys. J.* 56:151–60 (1989)). First, 200 µg of leuprolide acetate in 5 ml of aqueous solutions with methocel weight concentrations varying between 0% and 3.0% were vaginally administered. LHRH analog bioavailability was found to increase as methocel concentration increased to 1.75%, then to fall at higher methocel concentration (FIG. 2), mirroring a trend observed for receptormediated endocytosis with single cells (Edwards, et al., *Proc. Natl. Acad. Sci. U.S.A.* 93:1786–91 (1996)). This appears to suggest that transfer of LHRH analog into the systemic circulation is rate-limited by endocytic transfer from the apical side of the vaginal epithelium, which can itself be controlled by the viscosity of the methocel solution within which it is administered, for the fluid-mechanical reasons described above and in Edwards, et al., *Proc. Natl. Acad. Sci. U.S.A.* 93:1786–91(1996).

The enhanced bioavailability of LHRH also coincides with a longer-term release into the systemic circulation at the optimal methocel concentrations. This suggests the possibility of a diffusion-controlled delivery process, rather than an active, endocytic-controlled process; that is, increasing hydrogel viscosity might be related to diminished rate of peptide diffusion through the hydrogel to the vaginal epithelium. To test this hypothesis, the efficacy of a second, physically cross-linked hydrogel that was believed would not enhance endocytosis, but whose apparent viscosity (in the range of hydrogel concentrations 0.0–5.5%) was similar to that of the methocels (in the range 0.0–3.0%) was examined. It was anticipated that the physically cross-linked structure of the "control" hydrogel would prevent its deformation with (and entry into) invaginating sites on the epithelial membrane, hence impeding, rather than enhancing, endocytic uptake.

The results showed that when 5 ml of solution containing the physically cross-linked control gel was administered vaginally, the bioavailability of LHRH analog diminished with increasing concentration of the hydrogel in the range of 0.0–5.5%. Importantly, the duration of LHRH analog delivery also diminished with increasing control gel concentration, which is an unexpected effect if LHRH analog delivery is passive-diffusion controlled.

Figure 2:
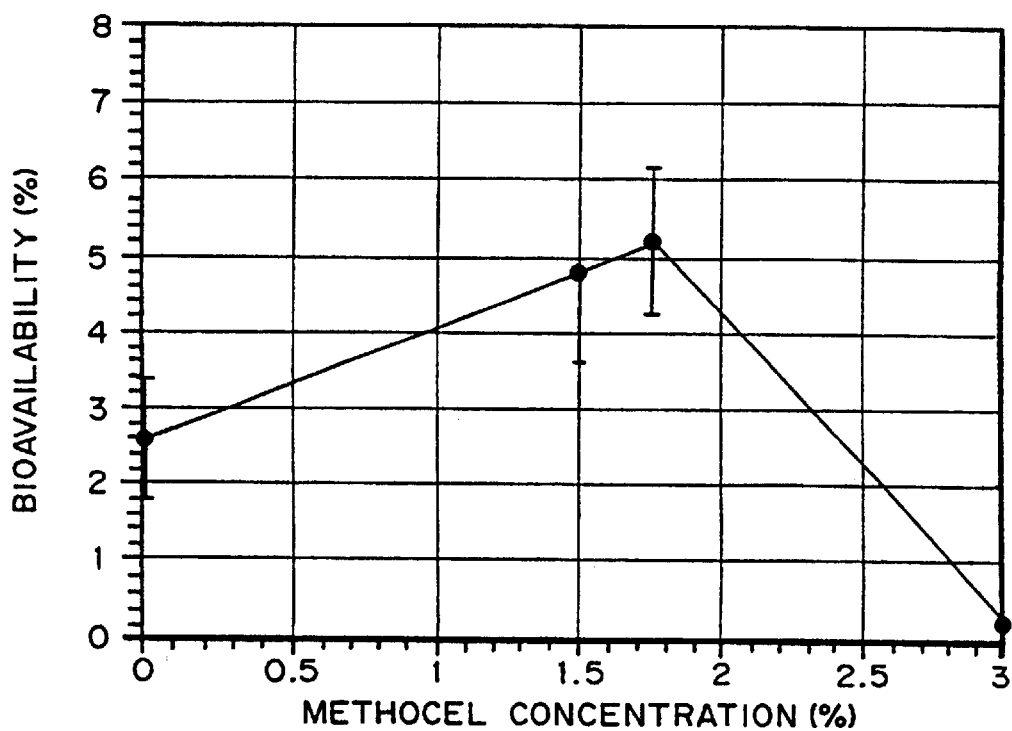
FIG. 2 is a graph showing bioavailability of LHRH analog following vaginal administration as a function of methyl cellulose ("methocel") concentration. Bioavailability is determined relative to intravenous injection (FIG. 1b) and is based on LH response. The administered dose of LHRH analog was 200 $\mu$g in 5 ml of methocel solution. Results are based on animals that responded to vaginal treatment, with standard error computed on the basis of n≧4. In all cases, less than 50% of treated animals responded with LH levels greater than 3 ng/ml for more than one sampling point, with sampling times of 0, 30, 60, 90, 120, 180, 240, 360, and 480 min.

To determine whether membrane damage might explain the results shown in FIG. 2, vasopressin was vaginally administered in methocel solutions of 1.5 and 1.75%. Identical to the saline vaginal administration (FIG. 1a), no detectable changes in concentrations of cortisol were observed when vasopressin was administered with the methocel solutions, indicating that the barrier properties of the membrane to passive transport remain intact.

C. Determination of Role of Steroids in Uptake and Transport

Biological response to vaginal LHRH analog administration exhibited a bimodal distribution in the studies (see FIG. 2), with approximately 30% of animals showing little or no response at all. No such bimodal response was observed when LHRH analog was administered by intravenous injection (FIG. 1b), indicating that the source of the bimodal response resides in the vaginal absorption pathway. It was therefore hypothesized that the responsiveness of animals to LHRH analog vaginal delivery varied with steroid-dependent hormone receptor expression (estrous cycle). To test this hypothesis, a group of ewes was ovariectomized and administered estradiol and progesterone to mimic the animals' estrous cycle. Ewes were pre-medicated with atropine (0.02 mg/lb) and Telazol (R) (2 mg/lb) intramuscularly. After induction of recumbency, thipental (5% in water) was administered intravenously to induce sufficient anesthesia to permit endotracheal intubation. Anesthesia was maintained using halothane in oxygen at 1–2 liters per minute. Ovaries were removed through a mid-line incision.

Within 24 h of surgery, a 1.5 cm silicone implant of estradiol (Compudose 200, Elanco, Ind.) was inserted into the left ear to provide a basal level of estradiol. The anestrus state was simulated after two weeks of estradiol delivery following surgery. Experiments were performed in the simulated anestrus state (i.e. two weeks after surgery) as described above. Immediately following the last blood sample, a progesterone-releasing intravaginal device (CIDR-G, Carter Hold Harvey Plastic Products, Hamilton, New Zealand) was inserted.

In a parallel study, an alternative progesterone-releasing device (Snychro-Mate-B, Sanofi Animal Health, Overland Park, Kans.) was placed in the left ear. The mid-luteal phase was simulated after permitting a 10 day intravaginal or ear progesterone treatment. Experiments were performed in the simulated mid-luteal phase as described above.

The progesterone-releasing (vaginal or ear) implant was removed and the follicular phase was simulated by allowing a time lapse of 48 h. Experiments were performed in the follicular phase as described above.

Figure 3:
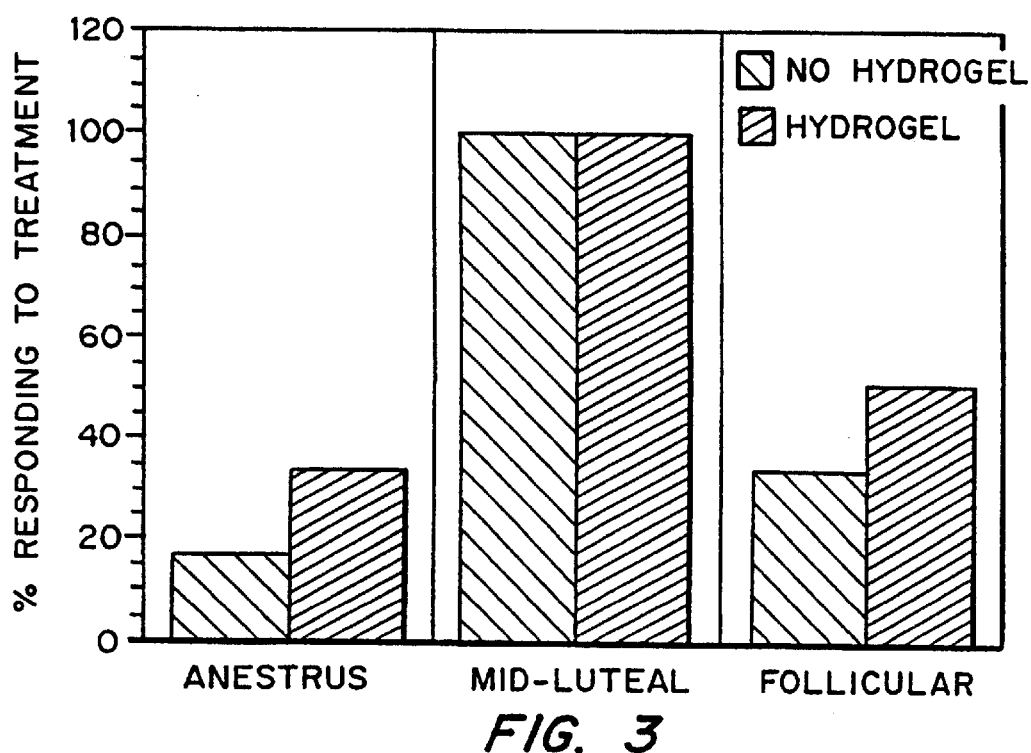
FIG. 3 is a graph showing the percent of responding animals to LHRH analog vaginal delivery as a function of (simulated) stage of the estrous cycle. Stage of estrous cycle was simulated by delivering estradiol for two weeks to ovariectomized ewes (anestrus phase), followed by two weeks of delivery of estradiol and progesterone (mid-luteal phase), followed by a period of 48 h after progesterone withdrawal (follicular phase). In each simulated phase, 10, 40, or 200 mg of LHRH analog were delivered vaginally in 5 ml of aqueous or methocel solution to groups of six ewes. Responding animals were defined as those treated animals with LH serum values exceeding 3 ng/ml for two or more sampling points, with sampling times of 0, 30, 60, 60, 120, 180, 240, 360, and 480 min.

Next, 200 µg of leuprolide acetate in 5 ml of aqueous solutions was vaginally administered during simulated anestrus (estradiol only), mid-luteal (estradiol and progesterone), and follicular (48 h after progesterone withdrawal) phases, as described above. When LHRH analog was delivered in aqueous solutions with or without 1.75% methocel, it was found that less than 50% of animals responded during estrogen replacement without progesterone. In contrast, 100% of animals responded when treated with progesterone and estradiol (FIG. 3). This same trend also was observed for the other LHRH analog doses. That is, a reproducible response was observed in all animals only during progesterone and estradiol treatment, when the animals can be expected to express maximal numbers of hormone receptors.

This confirms the hypothesis that the LH response of animals depended on steroid milieu, as is consistent with the hypothesis of uptake of LHRH analog occurs via a receptor-mediated route.

Figure 4:
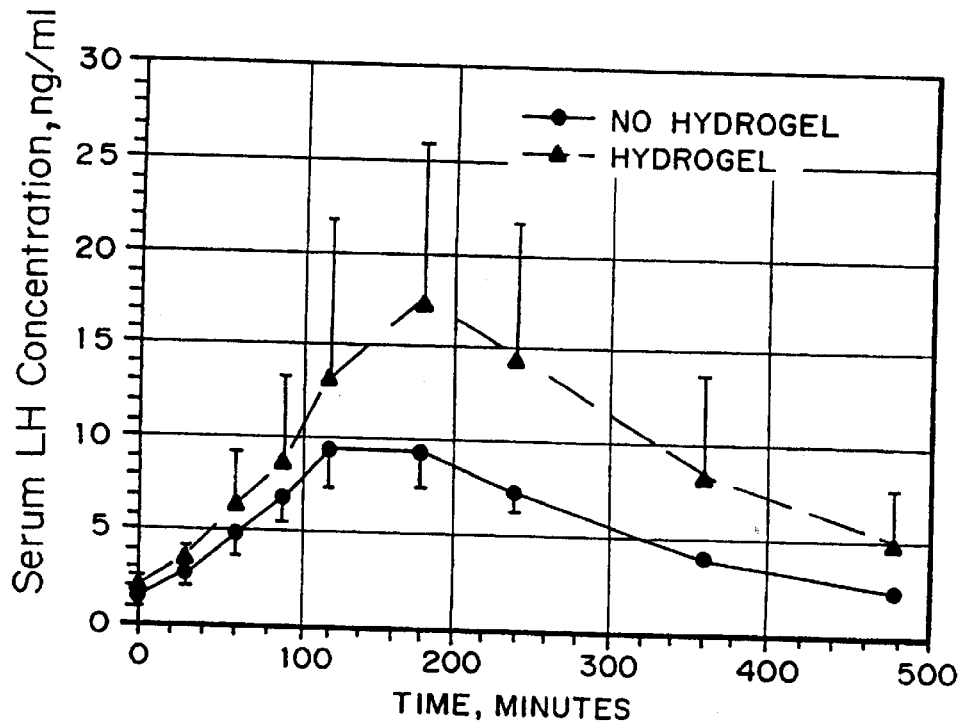
FIG. 4 is a graph showing serum LH response to vaginal administration of LHRH analog. LHRH analog was administered vaginally in ovariectomized ewes during the simulated mid-luteal phase in 5 ml of aqueous or methocel (1.75% methyl cellulose) solution (40 $\mu$g dose). Standard errors are based on n=6.
Figure 5:
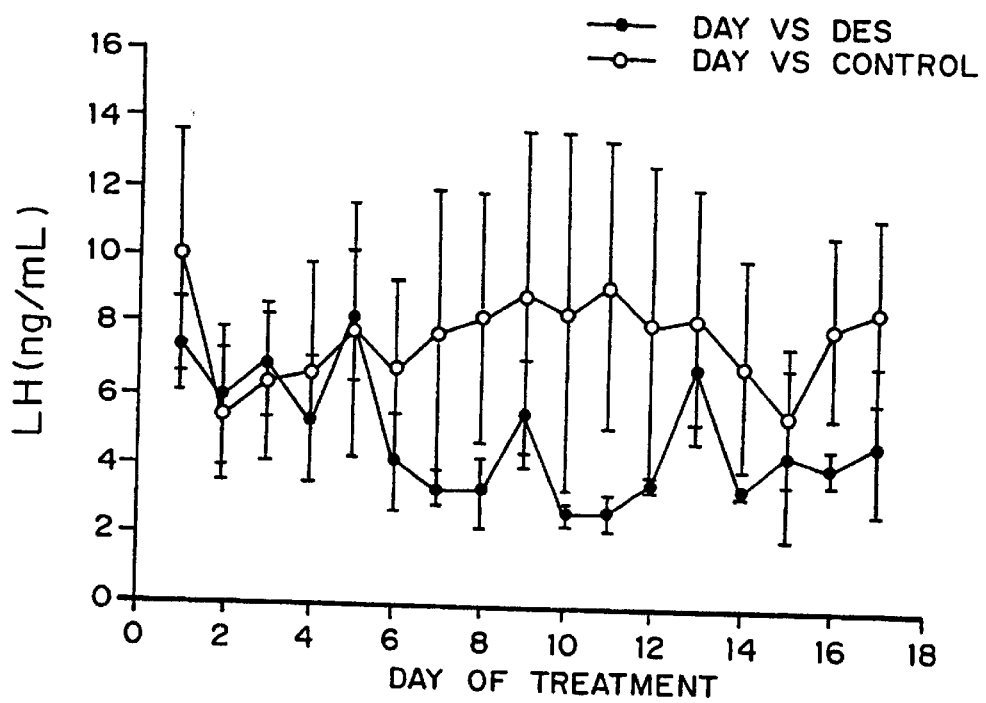
FIG. 5 is a graph of plasma LH concentration versus day of DES treatment.
Figure 6:
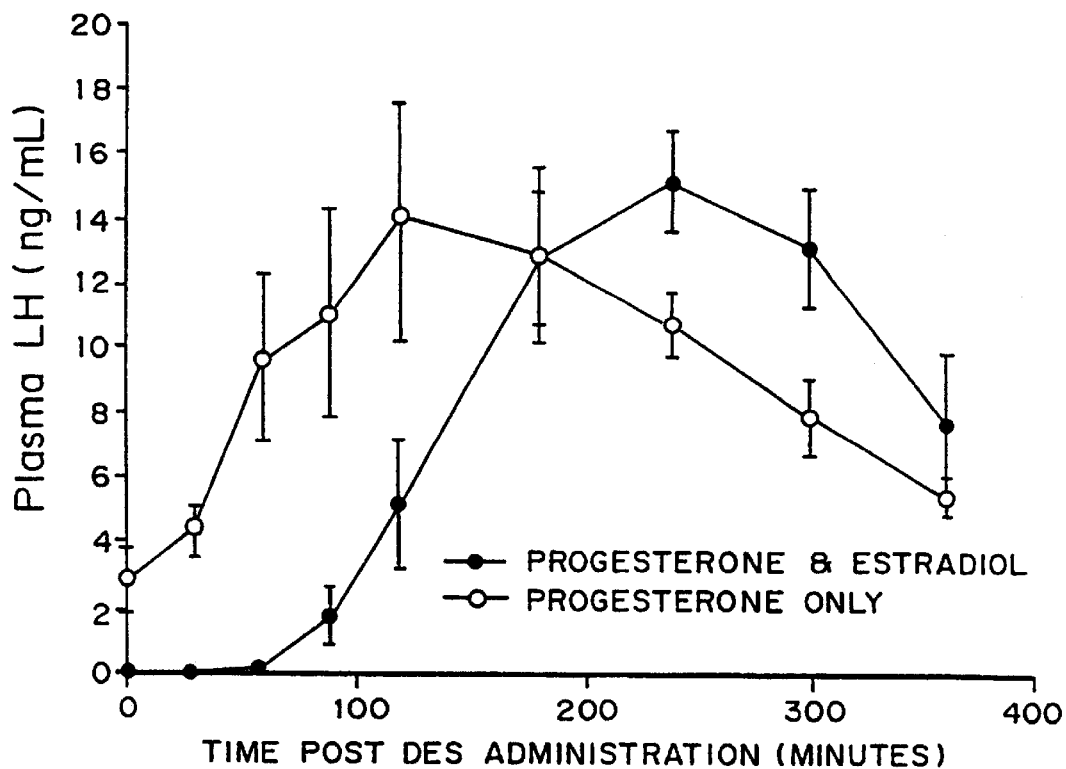
FIG. 6 is a graph of plasma LH concentration versus time following administration of DES, in combination with progesterone alone or progesterone and estradiol.

Three doses of LHRH analog: 10, 40, and 100 µg, were administered. It was found that during progesterone and estradiol treatment, the highest and lowest doses resulted in LH responses that were either saturated (maximal LH response with and without methocel) or undetectable, presumably due to the sigmoidal dose-response nature of LHRH analog treatment. The results of the intermediate dose-response study are shown in FIG. 4. The 1.75% methocel administration results in a bioavailability of 6% compared to 10% for the case of the 0% methocel. These results agree with the results of the uncontrolled animal study (FIG. 2) (minus non-responders).

A significant finding of this study is that LHRH analog delivery across the vaginal mucosa is receptor-mediated, with a reproducibility that can be increased by controlling the stage of the estrous cycle. This approach to be peptide delivery can be further improved by controlling the viscous properties of the medium that contacts the vaginal mucosa, and from which the peptide transfers. Unlike the single-cell systems where a similar phenomenon has been observed, the vaginal mucosa includes a mucus barrier that is itself highly viscous and presumably combines with the administered hydrogel to create a mixture of artificial and physiological hydrogels whose net viscous properties act to control the rate of vesicle formation along the apical epithelial membrane. While the exact nature of this mixed gel remains unclear (as, for example, the administration of estradiol and progesterone changes the rheological properties of the mucus lining, potentially providing an alternative interpretation of the results observed in FIG. 3), that hydrogel-enhancement of receptor-mediated transport can be achieved at vaginal mucosa suggests that a similar enhancement can achieved at other drug delivery sites, such as at the nasal mucosa.

The ability to enhance the delivery of LHRH analog into the systemic circulation by delivering LHRH analog in a "rheologically-optimized" hydrogel should help to make noninvasive LHRH analog therapies (such as the treatment of endometriosis or prostate cancer) more viable than at present. Recognition that it enters the body via a receptor-mediated route can further lead to hormonal-control strategies to minimize irreproducibility. Finally, the chemical attachment of LHRH analog to other molecules or nanoparticulate carriers that are too large to cross epithelial barriers of the body at a therapeutically relevant rate yet sufficiently small to enter an endocytic vesicle should make it possible to use LHRH analog as a kind of locomotive to propel other molecules, vesicle, or particles into the body without the need for injection.

EXAMPLE 2

Steroid and GnRH Transport

Studies were conducted to assess the involvement of steroids in modulating the transport of GNRH across the vaginal mucosa. The main objectives were to confirm the need for steroids in vaginal GnRH transport, to determine if treatment with both progesterone and estradiol were necessary, and to demonstrate down-regulation of LH secretion with daily administration of GnRH agonist.

A. Chronic Vaginal Dosing of DES to Suppress LH Secretion

The objective was to determine if chronic vaginal dosing with 200 µg of deslorelin ("DES") in gel would be able to suppress secretion of LH. Lower doses of DES will result in the down-regulation of the anterior pituitary gland in sheep. Ovariectomized sheep were used for the study, since they secrete high levels of LH in the absence of ovarian steroids. The sheep were dosed daily with DES in 5 mL of gel, or gel only for 17 days. A single blood sample was collected by jugular venipuncture. Plasma was collected and assayed for LH.

Results from this study are shown in FIG. 4. There were no differences in the average concentrations between the DES and control groups over the course of the study. LH secretion appears to have been slightly suppressed between days 6 and 12 of the study. However, a much greater inhibition in LH secretion was expected if significant amounts of DES were crossing the vaginal mucosa. An earlier study demonstrated that estrous cycles could be inhibited with daily vaginal administration of GnRH agonist. In this study, however, all the animals had intact ovaries. Previous studies have followed LH release after a single dosing. It has been shown that sheep treated with estradiol and progesterone respond much better in terms of the percentage of animals exhibiting LH release, the magnitude of the LH release, and a reduction in the variance of the response. Therefore, it is likely that treatment with progesterone, either alone or in combination with estradiol, was required for the GARH agonist to be transported across the vaginal mucosa.

B. Determination of Roles of Progesterone and Estradiol in Vaginal Transport

This study was conducted to determine if progesterone alone, or progesterone in combination with estradiol, is required to ensure GnRH transport across the vaginal epithelium. In past studies, estradiol was given as an implant inserted in the outer ear, which is a common method of administering estradiol to animals. However, it results in high and variable estradiol concentrations in jugular blood. It would be helpful to eliminate this steroid from the animal model, if possible, since delivering estradiol using GnRH-based technologies is of interest.

Ewes (n=12) were treated with progesterone using a vaginal CIDR device. In addition, six sheep received a 15 mm silastic implant of estradiol. Five days later, all sheep were treated vaginally with 200 µg of DES in gel. Blood samples were taken every 30 minutes for 2 hours following treatment and then every 60 minutes for an additional four hours.

All ewes in this experiment responded with a robust discharge of LH following GNRE treatment. There was a distinct difference in the pattern of LH release between the two groups (FIG. 13). The peak LH occurred earlier in ewes treated only with progesterone (120 minutes) than in ewes treated with progesterone and estradiol (240 minutes).

The difference in the timing of the peak LH between the groups is nearly identical to those differences between ovariectomized and ovariectomized plus estradiol treated ewes (see Deaver et al., Domest. Anim. Endocrinol. 4(2):95–102 (1987)). Thus, it is likely that the difference in the patterns of LH release is attributable to estradiol's effects on pituitary responsiveness to GnRH and not the vaginal uptake mechanism. Furthermore, if the latter were correct, then the lag time between treatment and vaginal transfer of GnRiRH into the circulatory system would be on the order of 7–80 minutes.

C. Effect of Vaginal Administration of DES in Progesterone-primed Ewes

The objective of this study was to determine if daily vaginal administration of DES in progestcrone-primed ewes would cause a reduction in basal LH secretion and loss of pituitary responsiveness of GnRH. Six ovariectomized ewes were used for the study. Vaginal CIDR devices containing progesterone were inserted. Twenty-four hours later, ewes were dosed daily with 200 µg of DES (GnRH agonist) in 5 mL of gel. Each day, blood samples were collected at 0 and 120 minutes post-treatment. These times were selected in order to evaluate changes in basal secretion of LH (time 0) and the peak LH response following GnRH administration (time 120).

The change in LH between 0 and 120 minutes was greatest in 3 of 6 ewes on the first day of DES administration. In the fourth ewe, a robust release of LH was observed following the first DES treatment, but the increase in LH was even higher following the second treatment with DES.

Figure 7:
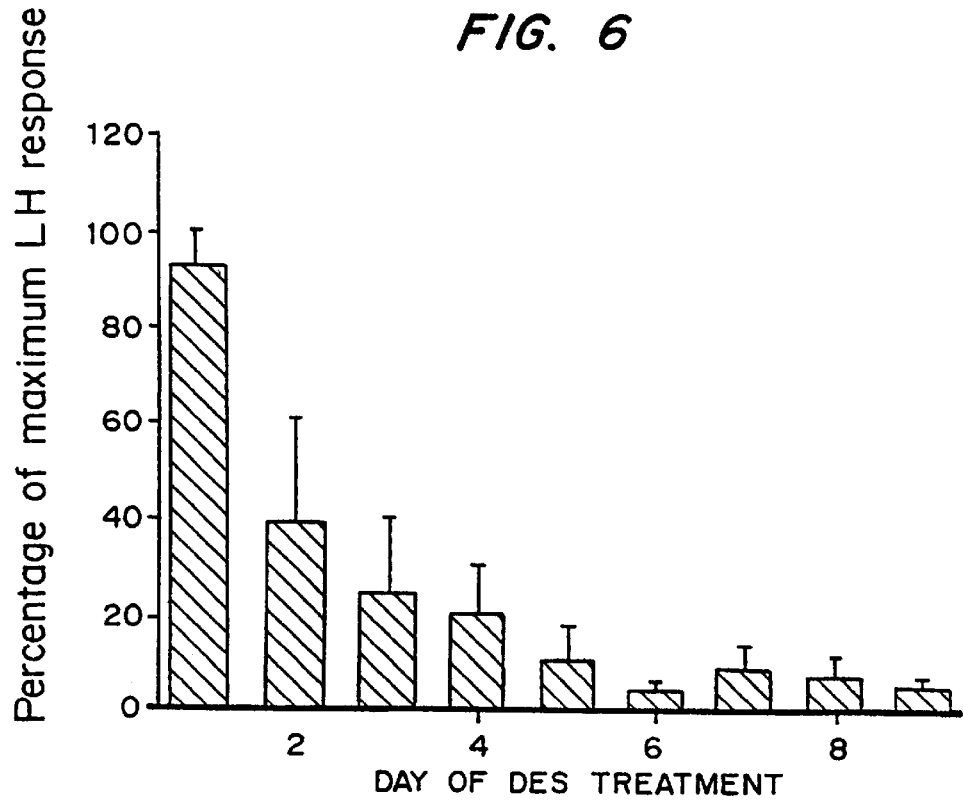
FIG. 7 is a graph of percentage of maximum LH response versus day of DES treatment for progesterone-primed ewes.
Figure 8:
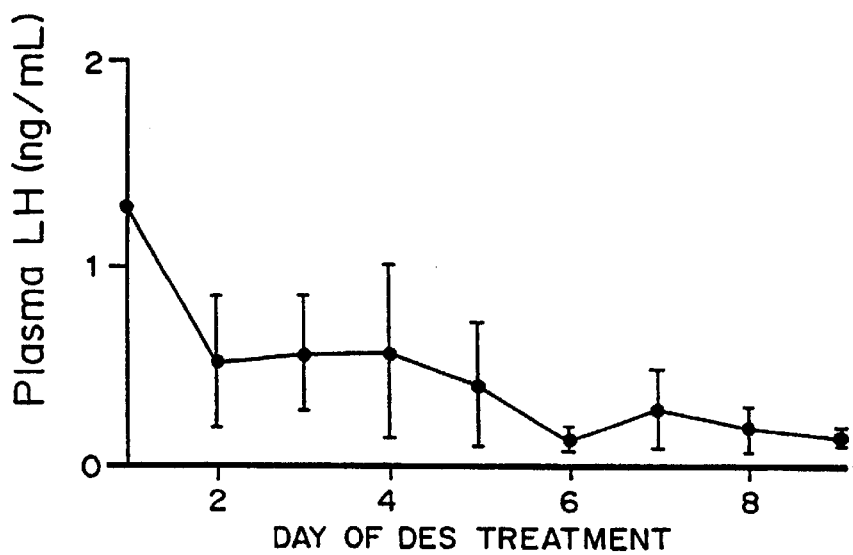
FIG. 8 is a graph of basal plasma LH concentration versus day of DES treatment for progesterone-primed ewes.
Figure 9:
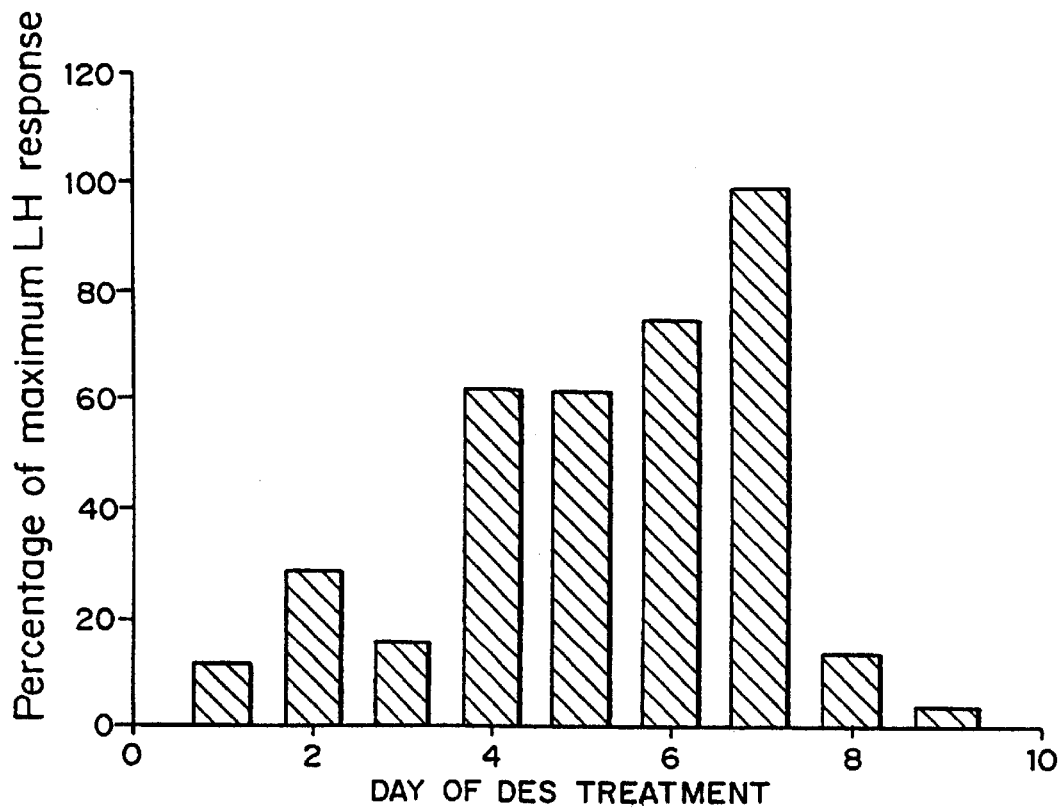
FIG. 9 is a graph of percentage of maximum LH response versus day of DES treatment for progesterone-primed ewes.

When the differential in LH release following the first treatment with DES is assigned a value of 100% and the change in responsiveness plotted against time (FIG. 7), it is clear that continued daily treatment significantly reduced pituitary responsiveness to DES. In addition, significant decreases in basal LH also occurred in these animals (FIG. 8).

In the two remaining animals, the change in LH secretion continued to increase 5 to 7 days following the initiation of DES treatment. However, once the maximum response was achieved, pituitary-responsiveness to DES rapidly declined (FIG. 16; Ewe 9). A reasonable interpretation of these data is that insufficient DES was transported over the first several days to initiate the down-regulation phenomena. However, once the transport mechanism became optimized, adequate transport of DES was achieved to down-regulate LH release from the anterior pituitary gland.

D. Direct Vaginal Administration of DES Enhanced Uptake

An attempt was made to treat ewes with progesterone using the systemic administration of a depot form of progesterone and ear implants of a synthetic progestogen. Pituitary release of LH was poor following the vaginal administration of DES in gel. When LH release in these animals was not observed, the gel from the same preparations used vaginally was injected subcutaneously. LH release was then obtained, confirming that the DES/gel preparations contained biologically active material. Given the consistent responses obtained in earlier experiments and those obtained more recently using the CIDR delivery system, it was concluded that the progesterone (generally) should be applied directly to the vagina in order to achieve sufficient local concentrations. Given that luteal phase sheep also respond well, systemic administration of greater amounts of progesterone than used here, in formulations that will maintain consistently high concentrations in the blood, should also work.

E. Controls Show Uptake is Selective.

Another study provided information about the role of the silastic CIDR device itself in the delivery process. The study was based on concern that the CIDR might be damaging the vaginal mucosa, allowing for GnRH transport by a non-selective mechanism. CIDR devices were inserted into six ewes. Five days later, all ewes were treated vaginally with DES. Five of the six ewes had a robust release of LH. After the initial dosing, three ewes were treated with DES and three with gel alone every day for 18 days. At the end of the 18-day treatment period, all ewes were again treated with DES in gel. This time, none of the ewes displayed a robust release of LH.

Review of the protocol and notes showed that the CIDR devices, which were designed to release progesterone only over a 10 to 12-day period, were not changed mid-way through the trial as initially planned. Consequently, by the time the second DES administration was given, the CIDR devices had been in place for approximately 24 days. The ewes therefore were no longer receiving adequate amounts of progesterone locally to maintain the vaginal transport system. This study showed that the CIDR per se does not facilitate vaginal uptake of GnRH.

Conclusions

Based on the outcome of all experiments, local short periods of progesterone treatment activates a mechanism for transporting GnRH agonist across the vaginal mucosa in sufficient amounts to acutely cause the release of LH and the down-regulation of LH release with repeated dosing.

Local exposure of the vagina to progesterone is preferred for the transport of GnRH agonist across the mucosal membrane. Systemic administration of either progesterone or synthetic progestogens is not preferred for achieving adequate priming of the vaginal mucosa for GnRH transport. Intravaginal devices used for administration of progesterone do not appear to directly effect vaginal transport of GnRH.

Approximately 50% of ewes will have significant transport after only 24 hours of exposure to progesterone, and essentially 100% of the ewes will transport GnRH after four days of exposure. Co-administration of estradiol will alter the time course of LH release in progesterone treated ewes, which likely is due to a direct effect on the anterior pituitary gland. The lag time is about 70–80 minutes between vaginal administration of GNRH and the transport of sufficient amounts of GNRH agonist into the blood to cause LH release. Chronic administration of GnRH agonist across the vaginal mucosa will reduce the basal secretion of LH and down-regulate the ability of the anterior pituitary gland to respond to GnRH agonist.

Those skilled in the art will recognize, or be able to ascertain using no more than routine experimentation, many equivalents to the specific embodiments of the invention described herein. The references cited herein are hereby incorporated by reference.

We claim:

1. A method for delivering an agent to cells at a site where uptake is desired comprising administering to the cells at the site where uptake is desired a composition comprising
   (a) a viscous material having an apparent viscosity between 10 and 2000 Poise and approximately the same apparent viscosity, at a shear stress of between approximately 1 and 200 Pascal at a strain rate approximately that of endocytosis, as the cytosolic fluid of the cell to which the agent is to be delivered,
   (b) a compound to be delivered, and
   (c) an enhancer in an amount effective to enhance expression of or binding to receptors eliciting receptor-mediated endocytosis on the cells at the site where uptake is desired.

2. The method of claim 1 wherein the enhancer is a steroid.

3. The method of claim 1 wherein the cells to which the compound is to be delivered are in the nose, rectum, mouth, ear, eye, or lungs.

4. The method of claim 1 wherein the composition is administered topically.

5. The method of claim 1 wherein the enhancer is administered systemically.

6. The method of claim 1 wherein the composition is administered to the vaginal mucosa.

7. The method of claim 1 wherein the compound to be delivered is selected from the group consisting of proteins, peptides, carbohydrates, nuceilc acid molecules, and chemotherapeutic agents.

8. The method of claim 7 wherein the enhancer is selected from the group consisting of hormones, glucocorticoids, and other molecules specifically binding to a receptor on a cell surface to induce endocytosis.

9. The method of claim 8 wherein the enhancer is a reproductive hormone.

10. The method of claim 1 wherein the enhancer is a glucocorticoid.

11. The method of claim 9 wherein the reproductive hormone is selected from the group consisting of progesterone, estradiol, and combinations thereof.

12. The method of claim 1 wherein the viscous material is selected from the group consisting of hydrogels, lipogels and sols.

13. The method of claim 12 wherein the hydrogel is selected from the group consisting of celluloses, polyalkyleneoxide, polyvinylpyrrolidone, dextrans, alginates, agaroses, gelatin, hyaluronic acid, trehalose, polyvinyl alcohol, and copolymers and blends thereof.

14. A composition for delivering an agent to cells at a site where uptake is desired comprising:
   (a) a viscous fluid having an apparent viscosity between 10 and 2000 Poise and approximately the same apparent viscosity, at a shear stress of between approximately 1 and 200 Pascal at a strain rate approximately that of endocytosis, as the cytosolic fluid of the cell to which the agent is to be delivered,
   (b) a compound to be delivered, and
   (c) an enhancer in an amount effective to enhance expression of or binding to receptors eliciting receptor-mediated endocytosis on the cells at the site where uptake is desired.

15. The composition of claim 14 in a formulation suitable for administration to mucosa of tissue selected from group consisting of the nose, the rectum, the mouth, the ear, the eye, and the lungs.

16. The composition of claim 14 wherein the compound to be delivered is selected from the group consisting of proteins, peptides, carbohydrates, nucleic acid molecules, and chemotherapeutic agents.

17. The composition of claim 14 wherein the enhancer is selected from the group consisting of hormones and glucocorticoids.

18. The composition of claim 14 wherein the hormone is a reproductive hormone.

19. The composition of claim 14 wherein the viscous material is selected from the group consisting of hydrogels, lipogels and sols.

20. The composition of claim 19 wherein the hydrogel is selected from the group consisting of celluloses, polyalkyleneoxide, polyvinylpyrrolidone, dextrans, alginates, agaroses, gelatin, hyaluronic acid, trehalose, polyvinyl alcohol, and copolymers and blends thereof.

21. A kit for delivering a compound to cells comprising:
   a first composition comprising a viscous fluid and the compound to be delivered, wherein the viscous fluid has an apparent viscosity between 10 and 2000 Poise and approximately the same apparent viscosity, at a shear stress of between approximately 1 and 200 Pascal at a strain rate approximately that of endocytosis, as the cytosolic fluid of the cell to which the agent is to be delivered, and
   a second composition comprising an enhancer in an amount effective to enhance expression of receptors eliciting receptor-mediated endocytosis on the cells, thereby to enhance receptor mediated endocytosis of the agent into the cells.

22. The kit of claim 21 wherein the second composition is in a formulation suitable for topical or systemic administration.

* * * * *